(12) United States Patent
Eschbach et al.

(10) Patent No.: US 10,631,945 B2
(45) Date of Patent: Apr. 28, 2020

(54) AUTOCLAVABLE LOAD SENSING DEVICE

(71) Applicant: Covidien LP, Mansfield, MA (US)

(72) Inventors: Matthew Eschbach, Cheshire, CT (US); Russell Pribanic, Roxbury, CT (US)

(73) Assignee: COVIDIEN LP, Mansfield, MA (US)

( * ) Notice: Subject to any disclaimer, the term of this patent is extended or adjusted under 35 U.S.C. 154(b) by 154 days.

(21) Appl. No.: 15/886,958

(22) Filed: Feb. 2, 2018

(65) Prior Publication Data

US 2018/0243042 A1 Aug. 30, 2018

Related U.S. Application Data

(60) Provisional application No. 62/464,707, filed on Feb. 28, 2017.

(51) Int. Cl.
*A61B 90/00* (2016.01)
*A61B 17/00* (2006.01)
(Continued)

(52) U.S. Cl.
CPC ........ *A61B 90/06* (2016.02); *A61B 17/00234* (2013.01); *A61B 17/07207* (2013.01); *G01L 5/0061* (2013.01); *A61B 2017/00017* (2013.01); *A61B 2017/00022* (2013.01); *A61B 2017/0046* (2013.01); *A61B 2017/00398* (2013.01); *A61B 2017/00473* (2013.01); *A61B 2017/00486* (2013.01); *A61B 2017/00734* (2013.01); *A61B 2090/064* (2016.02);
(Continued)

(58) Field of Classification Search
CPC ....... G01L 1/2237; G01L 1/2225; G01L 1/22; G01L 1/20
See application file for complete search history.

(56) References Cited

U.S. PATENT DOCUMENTS

| | | |
|---|---|---|
| 2,777,340 A | 1/1957 | Hettwer et al. |
| 2,952,807 A | 9/1960 | Heller |

(Continued)

FOREIGN PATENT DOCUMENTS

| | | |
|---|---|---|
| CA | 2451558 A1 | 1/2003 |
| CN | 1547454 A | 11/2004 |

(Continued)

OTHER PUBLICATIONS

"Wheatstone bridge," https://en.wikipedia.org/wiki/Wheatstone_bridge , accessed Aug. 28, 2019. (Year: 2019).*

(Continued)

*Primary Examiner* — Michael W Kahelin

(57) ABSTRACT

An adapter for interconnecting a surgical end effector to a surgical device includes: a drive shaft; and a load sensing device disposed about the draft shaft, the load sensing device configured to measure strain imparted on the drive shaft. The load sensing device includes a housing having: a tubular portion having a first end and a second end and defining a cavity therebetween; a first end cap disposed at the first end, the first end cap having a first opening; and a second end cap disposed at the second end, the second end cap having a second opening. The load sensing device also includes a conductive element wrapped at least partially about the tubular portion.

20 Claims, 9 Drawing Sheets

(51) Int. Cl.
*G01L 5/00* (2006.01)
*A61B 17/072* (2006.01)
(52) U.S. Cl.
CPC .......... *A61B 2090/0813* (2016.02); *A61B 2562/0252* (2013.01); *A61B 2562/0261* (2013.01)

(56) References Cited

U.S. PATENT DOCUMENTS

| | | |
|---|---|---|
| 2,957,353 A | 10/1960 | Babacz |
| 3,036,283 A | 5/1962 | Singdale et al. |
| 3,111,328 A | 11/1963 | Di Rito et al. |
| 3,695,058 A | 10/1972 | Keith, Jr. |
| 3,734,515 A | 5/1973 | Dudek |
| 3,759,336 A | 9/1973 | Marcovitz et al. |
| 4,162,399 A | 7/1979 | Hudson |
| 4,606,343 A | 8/1986 | Conta et al. |
| 4,705,038 A | 11/1987 | Sjostrom et al. |
| 4,722,685 A | 2/1988 | de Estrada et al. |
| 4,823,807 A | 4/1989 | Russell et al. |
| 4,874,181 A | 10/1989 | Hsu |
| 5,129,118 A | 7/1992 | Walmesley |
| 5,129,570 A | 7/1992 | Schulze et al. |
| 5,152,744 A | 10/1992 | Krause et al. |
| 5,301,061 A | 4/1994 | Nakada et al. |
| 5,312,023 A | 5/1994 | Green et al. |
| 5,326,013 A | 7/1994 | Green et al. |
| 5,350,355 A | 9/1994 | Sklar |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,400,267 A | 3/1995 | Denen |
| 5,411,508 A | 5/1995 | Bessler et al. |
| 5,413,267 A | 5/1995 | Solyntjes et al. |
| 5,427,087 A | 6/1995 | Ito et al. |
| 5,433,721 A | 7/1995 | Hooven et al. |
| 5,467,911 A | 11/1995 | Tsuruta et al. |
| 5,476,379 A | 12/1995 | Disel |
| 5,487,499 A | 1/1996 | Sorrentino et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,549,637 A | 8/1996 | Crainich |
| 5,553,675 A | 9/1996 | Pitzen et al. |
| 5,562,239 A | 10/1996 | Boiarski et al. |
| 5,564,615 A | 10/1996 | Bishop et al. |
| 5,609,560 A | 3/1997 | Ichikawa et al. |
| 5,626,587 A | 5/1997 | Bishop et al. |
| 5,632,432 A | 5/1997 | Schulze et al. |
| 5,645,209 A | 7/1997 | Green et al. |
| 5,647,526 A | 7/1997 | Green et al. |
| 5,653,374 A | 8/1997 | Young et al. |
| 5,658,300 A | 8/1997 | Bito et al. |
| 5,662,662 A | 9/1997 | Bishop et al. |
| 5,667,517 A | 9/1997 | Hooven |
| 5,693,042 A | 12/1997 | Boiarski et al. |
| 5,704,534 A | 1/1998 | Huitema et al. |
| 5,713,505 A | 2/1998 | Huitema |
| 5,762,603 A | 6/1998 | Thompson |
| 5,779,130 A | 7/1998 | Alesi et al. |
| 5,782,396 A | 7/1998 | Mastri et al. |
| 5,782,397 A | 7/1998 | Koukline |
| 5,792,573 A | 8/1998 | Pitzen et al. |
| 5,797,536 A | 8/1998 | Smith et al. |
| 5,820,009 A | 10/1998 | Melling et al. |
| 5,863,159 A | 1/1999 | Lasko |
| 5,908,427 A | 6/1999 | McKean et al. |
| 5,954,259 A | 9/1999 | Viola et al. |
| 5,964,774 A | 10/1999 | McKean et al. |
| 5,993,454 A | 11/1999 | Longo |
| 6,010,054 A | 1/2000 | Johnson et al. |
| 6,017,354 A | 1/2000 | Culp et al. |
| 6,032,849 A | 3/2000 | Mastri et al. |
| 6,045,560 A | 4/2000 | McKean et al. |
| 6,090,123 A | 7/2000 | Culp et al. |
| 6,126,651 A | 10/2000 | Mayer |
| 6,129,547 A | 10/2000 | Cise et al. |
| 6,165,169 A | 12/2000 | Panescu et al. |
| 6,239,732 B1 | 5/2001 | Cusey |
| 6,241,139 B1 | 6/2001 | Milliman et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,315,184 B1 | 11/2001 | Whitman |
| 6,321,855 B1 | 11/2001 | Barnes |
| 6,329,778 B1 | 12/2001 | Culp et al. |
| 6,343,731 B1 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,434,507 B1 | 8/2002 | Clayton et al. |
| 6,443,973 B1 | 9/2002 | Whitman |
| 6,461,372 B1 | 10/2002 | Jensen et al. |
| 6,488,197 B1 | 12/2002 | Whitman |
| 6,491,201 B1 | 12/2002 | Whitman |
| 6,533,157 B1 | 3/2003 | Whitman |
| 6,537,280 B2 | 3/2003 | Dinger et al. |
| 6,610,066 B2 | 8/2003 | Dinger et al. |
| 6,611,793 B1 | 8/2003 | Burnside et al. |
| 6,645,218 B1 | 11/2003 | Cassidy et al. |
| 6,654,999 B2 | 12/2003 | Stoddard et al. |
| 6,698,643 B2 | 3/2004 | Whitman |
| 6,699,177 B1 | 3/2004 | Wang et al. |
| 6,716,233 B1 | 4/2004 | Whitman |
| 6,743,240 B2 | 6/2004 | Smith et al. |
| 6,783,533 B2 | 8/2004 | Green et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,860,892 B1 | 3/2005 | Tanaka et al. |
| 6,899,538 B2 | 5/2005 | Matoba |
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,111,769 B2 | 9/2006 | Wales et al. |
| 7,122,029 B2 | 10/2006 | Koop et al. |
| 7,140,528 B2 | 11/2006 | Shelton, IV |
| 7,141,049 B2 | 11/2006 | Stern et al. |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |
| 7,252,660 B2 | 8/2007 | Kunz |
| 7,328,828 B2 | 2/2008 | Ortiz et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |

(56) References Cited

U.S. PATENT DOCUMENTS

| | | |
|---|---|---|
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Klueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,900,805 B2 | 3/2011 | Shelton, IV et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,011,550 B2 | 9/2011 | Aranyi et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,114,118 B2 | 2/2012 | Knodel et al. |
| 8,127,975 B2 | 3/2012 | Olson et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,342,379 B2 | 1/2013 | Whitman et al. |
| 8,348,130 B2 | 1/2013 | Shah et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,403,926 B2 | 3/2013 | Nobis et al. |
| 8,418,904 B2 | 4/2013 | Wenchell et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,523,043 B2 | 9/2013 | Ullrich et al. |
| 8,551,076 B2 | 10/2013 | Duval et al. |
| 8,561,871 B2 | 10/2013 | Rajappa et al. |
| 8,561,874 B2 | 10/2013 | Scirica |
| 8,602,287 B2 | 12/2013 | Yates et al. |
| 8,623,000 B2 | 1/2014 | Humayun et al. |
| 8,627,995 B2 | 1/2014 | Smith et al. |
| 8,632,463 B2 | 1/2014 | Drinan et al. |
| 8,636,766 B2 | 1/2014 | Milliman et al. |
| 8,647,258 B2 | 2/2014 | Aranyi et al. |
| 8,652,121 B2 | 2/2014 | Quick et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,715,306 B2 | 5/2014 | Faller et al. |
| 8,758,391 B2 | 6/2014 | Swayze et al. |
| 8,806,973 B2 | 8/2014 | Ross et al. |
| 8,808,311 B2 | 8/2014 | Heinrich et al. |
| 8,820,605 B2 | 9/2014 | Shelton, IV |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,888,762 B2 | 11/2014 | Whitman |
| 8,893,946 B2 | 11/2014 | Boudreaux et al. |
| 8,899,462 B2 | 12/2014 | Kostrzewski et al. |
| 8,905,289 B2 | 12/2014 | Patel et al. |
| 8,919,630 B2 | 12/2014 | Milliman |
| 8,931,680 B2 | 1/2015 | Milliman |
| 8,939,344 B2 | 1/2015 | Olson et al. |
| 8,950,646 B2 | 2/2015 | Viola |
| 8,960,519 B2 | 2/2015 | Whitman et al. |
| 8,961,396 B2 | 2/2015 | Azarbarzin et al. |
| 8,967,443 B2 | 3/2015 | McCuen |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,016,545 B2 | 4/2015 | Aranyi et al. |
| 9,023,014 B2 | 5/2015 | Chowaniec et al. |
| 9,033,868 B2 | 5/2015 | Whitman et al. |
| 9,055,943 B2 | 6/2015 | Zemlok et al. |
| 9,064,653 B2 | 6/2015 | Prest et al. |
| 9,072,515 B2 | 7/2015 | Hall et al. |
| 9,113,847 B2 | 8/2015 | Whitman et al. |
| 9,113,875 B2 | 8/2015 | Viola et al. |
| 9,113,876 B2 | 8/2015 | Zemlok et al. |
| 9,113,899 B2 | 8/2015 | Garrison et al. |
| 9,216,013 B2 | 12/2015 | Scirica et al. |
| 9,241,712 B2 | 1/2016 | Zemlok et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 2001/0031975 A1 | 10/2001 | Whitman et al. |
| 2002/0049454 A1 | 4/2002 | Whitman et al. |
| 2002/0165541 A1 | 11/2002 | Whitman |
| 2003/0038938 A1 | 2/2003 | Jung et al. |
| 2003/0165794 A1 | 9/2003 | Matoba |
| 2004/0034369 A1 | 2/2004 | Sauer et al. |
| 2004/0111012 A1 | 6/2004 | Whitman |
| 2004/0133189 A1 | 7/2004 | Sakurai |
| 2004/0153124 A1 | 8/2004 | Whitman |

(56) References Cited

U.S. PATENT DOCUMENTS

| | | |
|---|---|---|
| 2004/0176751 A1 | 9/2004 | Weitzner et al. |
| 2004/0193146 A1 | 9/2004 | Lee et al. |
| 2005/0125027 A1 | 6/2005 | Knodel et al. |
| 2005/0131442 A1 | 6/2005 | Yachia et al. |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0259073 A1 | 11/2006 | Miyamoto et al. |
| 2006/0278680 A1 | 12/2006 | Viola et al. |
| 2006/0284730 A1 | 12/2006 | Schmid et al. |
| 2007/0023476 A1 | 2/2007 | Whitman et al. |
| 2007/0023477 A1 | 2/2007 | Whitman et al. |
| 2007/0027469 A1 | 2/2007 | Smith et al. |
| 2007/0029363 A1 | 2/2007 | Popov |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0270784 A1 | 11/2007 | Smith et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0147089 A1 | 6/2008 | Loh et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0012533 A1 | 1/2009 | Barbagli et al. |
| 2009/0090763 A1 | 4/2009 | Zemlok et al. |
| 2009/0099876 A1 | 4/2009 | Whitman |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0209946 A1 | 8/2009 | Swayze et al. |
| 2009/0209990 A1 | 8/2009 | Yates et al. |
| 2009/0254094 A1 | 10/2009 | Knapp et al. |
| 2009/0299141 A1 | 12/2009 | Downey et al. |
| 2010/0023022 A1 | 1/2010 | Zeiner et al. |
| 2010/0069942 A1 | 3/2010 | Shelton, IV |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2011/0071508 A1 | 3/2011 | Duval et al. |
| 2011/0077673 A1 | 3/2011 | Grubac et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174009 A1 | 7/2011 | Iizuka et al. |
| 2011/0174099 A1 | 7/2011 | Ross et al. |
| 2011/0184245 A1 | 7/2011 | Xia et al. |
| 2011/0204119 A1 | 8/2011 | McCuen |
| 2011/0218522 A1 | 9/2011 | Whitman |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0074199 A1 | 3/2012 | Olson et al. |
| 2012/0089131 A1 | 4/2012 | Zemlok et al. |
| 2012/0104071 A1 | 5/2012 | Bryant |
| 2012/0116368 A1 | 5/2012 | Viola |
| 2012/0143002 A1 | 6/2012 | Aranyi et al. |
| 2012/0172924 A1 | 7/2012 | Allen, IV |
| 2012/0211542 A1 | 8/2012 | Racenet |
| 2012/0223121 A1 | 9/2012 | Viola et al. |
| 2012/0245428 A1 | 9/2012 | Smith et al. |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0093149 A1 | 4/2013 | Saur et al. |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0236174 A1 | 8/2014 | Williams et al. |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0365235 A1 | 12/2014 | DeBoer et al. |
| 2014/0373652 A1 | 12/2014 | Zergiebel et al. |
| 2015/0014392 A1 | 1/2015 | Williams et al. |
| 2015/0048144 A1 | 2/2015 | Whitman |
| 2015/0076205 A1 | 3/2015 | Zergiebel |
| 2015/0080912 A1 | 3/2015 | Sapre |
| 2015/0112381 A1 | 4/2015 | Richard |
| 2015/0122870 A1 | 5/2015 | Zemlok et al. |
| 2015/0133224 A1 | 5/2015 | Whitman et al. |
| 2015/0150547 A1 | 6/2015 | Ingmanson et al. |
| 2015/0150574 A1 | 6/2015 | Richard et al. |
| 2015/0157320 A1 | 6/2015 | Zergiebel et al. |
| 2015/0157321 A1 | 6/2015 | Zergiebel et al. |
| 2015/0164502 A1 | 6/2015 | Richard et al. |
| 2015/0201931 A1 | 7/2015 | Zergiebel et al. |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |
| 2016/0106406 A1 | 4/2016 | Cabrera et al. |
| 2016/0113648 A1 | 4/2016 | Zergiebel et al. |
| 2016/0113649 A1 | 4/2016 | Zergiebel et al. |

FOREIGN PATENT DOCUMENTS

| | | |
|---|---|---|
| CN | 1957854 A | 5/2007 |
| CN | 101495046 A | 7/2009 |
| CN | 102247182 A | 11/2011 |

(56) References Cited

FOREIGN PATENT DOCUMENTS

| | | | |
|---|---|---|---|
| DE | 102008053842 A1 | 5/2010 |
| EP | 0705571 A1 | 4/1996 |
| EP | 1563793 A1 | 8/2005 |
| EP | 1769754 A1 | 4/2007 |
| EP | 2316345 A1 | 5/2011 |
| EP | 2668910 A2 | 12/2013 |
| EP | 2959842 A1 | 12/2015 |
| EP | 3064141 A1 | 9/2016 |
| ES | 2333509 A1 | 2/2010 |
| JP | 2005-125075 A | 5/2005 |
| KR | 20120022521 A | 3/2012 |
| WO | 2011/108840 A2 | 9/2011 |
| WO | 2012/040984 A1 | 4/2012 |

OTHER PUBLICATIONS

Extended European Search Report corresponding to International Application No. EP 14 18 4882.0 dated May 12, 2015.
Canadian Office Action corresponding to International Application No. CA 2640399 dated May 7, 2015.
Japanese Office Action corresponding to International Application No. JP 2011-197365 dated Mar. 23, 2015.
Japanese Office Action corresponding to International Application No. JP 2011-084092 dated May 20, 2015.
Japanese Office Action corresponding to International Application No. JP 2014-148482 dated Jun. 2, 2015.
Extended European Search Report corresponding to International Application No. EP 14 18 9358.6 dated Jul. 8, 2015.
Extended European Search Report corresponding to International Application No. EP 14 19 6148.2 dated Apr. 23, 2015.
Partial European Search Report corresponding to International Application No. EP 14 19 6704.2 dated May 11, 2015.
Australian Office Action corresponding to International Application No. AU 2010241367 dated Aug. 20, 2015.
Partial European Search Report corresponding to International Application No. EP 14 19 9783.3 dated Sep. 3, 2015.
Extended European Search Report corresponding to International Application No. EP 15 16 9962.6 dated Sep. 14, 2015.
Extended European Search Report corresponding to International Application No. EP 15 15 1076.5 dated Apr. 22, 2015.
Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, dated Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
Chinese Office Action corresponding to counterpart Int, Appin. No. CN 201310369318.2 dated Jun. 28, 2016.
Chinese Office Action (with English translation), dated Jul. 4, 2016, corresponding to Chinese Patent Application No. 2015101559718; 23 total pages.
European Search Report EP 15 156 035.6 dated Aug. 10, 2016.
European Search Report corresponding to EP 15 184 915.5-1654 dated Sep. 16, 2016.
Australian Examination Report No. 1 corresponding to International Application No. AU 2013205872 dated Oct. 19, 2016.
Australian Examination Report from Appl. No. AU 2013205840 dated Nov. 3, 2016.
European Search Report dated Jun. 27, 2018 issued in corresponding EP Appln. No. 18159010.0.
European Examination Report dated Aug. 26, 2019 issued in corresponding EP Appln. No. 18159010.0.

\* cited by examiner

AUTOCLAVABLE LOAD SENSING DEVICE

CROSS-REFERENCE TO RELATED APPLICATIONS

This application claims the benefit of and priority to U.S. Provisional Patent Application No. 62/464,707, filed Feb. 28, 2017, the entire disclosure of which is incorporated by reference herein.

BACKGROUND

1. Technical Field

The present disclosure relates to surgical devices. More specifically, the present disclosure relates to handheld electromechanical surgical systems for performing surgical procedures having reusable components with load sensing devices.

2. Background of Related Art

Linear clamping, cutting and stapling devices are used in surgical procedures to resect cancerous or anomalous tissue from a gastro-intestinal tract. Conventional linear clamping, cutting and stapling instruments include a pistol grip-styled structure having an elongated shaft and an end effector having a pair of gripping members disposed at a distal end of the shaft to clamp, cut, and staple tissue. Actuation of the gripping members is usually accomplished by actuating a trigger coupled to the handle, in response to which one of the two gripping members, such as the anvil portion, moves or pivots relative to the elongated shaft while the other gripping element remains fixed. The fixed gripping member includes a staple cartridge and a mechanism for ejecting the staples through the clamped tissue against the anvil portion, thereby stapling the tissue. The end effector may be integrally formed with the shaft or may be detachable allowing for interchangeability of various gripping and stapling members.

A number of surgical device manufacturers have also developed proprietary powered drive systems for operating and/or manipulating the end effectors. The powered drive systems may include a powered handle assembly, which may be reusable, and a disposable end effector that is removably connected to the powered handle assembly.

Many of the existing end effectors for use with existing powered surgical devices and/or handle assemblies are driven by a linear driving force. For example, end effectors for performing endo-gastrointestinal anastomosis procedures, end-to-end anastomosis procedures and transverse anastomosis procedures, are actuated by a linear driving force. As such, these end effectors are not compatible with surgical devices and/or handle assemblies that use rotary motion.

In order to make the linear driven end effectors compatible with powered surgical devices that use a rotary motion to deliver power, a need exists for adapters to interconnect the linear driven end effectors with the powered rotary driven surgical devices. These adapters may also be reusable, and as such, need to able to withstand multiple sterilization cycles.

As these adapters are becoming more sophisticated and include various electronic components, there is a need for electronic components disposed within the adapters that can withstand multiple autoclave cycles.

SUMMARY

Powered surgical devices may include various sensors for providing feedback during their operation. However, one limitation of the electronics and sensors used in the sterile environment of the operating room is that they need to be designed to withstand multiple cleaning and autoclave cycles. In order to gather information of the mechanical forces applied by the powered surgical devices, load sensing devices, such as load cells having strain gauges, are disposed on one or more mechanical components of the powered surgical device and/or adapters coupled thereto. Conventional strain gauges include a wire disposed on a substrate with wire leads exiting from the substrate. In addition, strain gauges also include multiple solder points and substrate interfaces between the wire and the substrate. Thus, conventional strain gauges can potentially fail when they are subjected to sterilization processes which may include exposure to harsh chemicals and/or high temperature. In particular, substrate interfaces and solder points in conventional strain gauges may delaminate or develop boundary stresses due to material property changes as the stain gauge is exposed to high temperatures. Boundary stresses can sever electrical connectors and/or allow liquid to enter the electrical circuit and result in a short circuit. The present disclosure provides a load sensing device that has no bonded substrate interfaces thereby avoiding failure modes associated with conventional strain gauge load cells. In addition, all of the circuit components are disposed outside the load sensing device.

According to one embodiment of the present disclosure, an adapter for interconnecting a surgical end effector to a surgical device is disclosed. The adapter includes: a drive shaft; and a load sensing device disposed about the draft shaft, the load sensing device configured to measure strain imparted on the drive shaft. The load sensing device includes a housing having: a tubular portion having a first end and a second end and defining a cavity therebetween; a first end cap disposed at the first end, the first end cap having a first opening; and a second end cap disposed at the second end, the second end cap having a second opening. The load sensing device also includes a conductive element wrapped at least partially about the tubular portion.

According to another embodiment of the present disclosure, a surgical system is disclosed. The surgical system includes a handheld surgical device including a motor, a power source coupled to the motor, and a controller configured to control the motor; and an adapter configured to couple to the surgical device. The adapter includes: a drive shaft configured to couple to and movable by the motor; and a load sensing device disposed about the draft shaft, the load sensing device configured to measure strain imparted on the drive shaft. The load sensing device includes a housing having: a tubular portion having a first end and a second end and defining a cavity therebetween; a first end cap disposed at the first end, the first end cap having a first opening; and a second end cap disposed at the second end, the second end cap having a second opening. The load sensing device also includes a conductive element wrapped at least partially about the tubular portion.

According to one aspect of any of the above embodiments, the adapter includes a strain sensor circuit coupled to the conductive element, the strain sensor circuit configured to output an electrical signal corresponding to the strain imparted on the drive shaft. The strain sensor circuit may include a resistor network having a plurality of resistive arms and the conductive element may be one of the plurality of resistive arms.

According to another embodiment of the present disclosure, a load sensing device includes a housing having: a tubular portion having a first end and a second end and defining a cavity therebetween; a first end cap disposed at the first end, the first end cap having a first opening; and a second end cap disposed at the second end, the second end cap having a second opening. The load sensing device also includes a conductive element wrapped at least partially about the tubular portion.

According to one aspect of any of the above embodiments, each of the first end cap and the second end cap has a frustoconical shape.

According to another aspect of any of the above embodiments, the tubular portion may include a pair of radially extending lips defining an annular groove therebetween.

According to a further aspect of any of the above embodiments, the conductive element may be disposed within the annular groove. The conductive element may include an insulative sheath.

According to one aspect of any of the above embodiments, a potting material is disposed within the annular groove.

BRIEF DESCRIPTION OF THE DRAWINGS

Embodiments of the present disclosure are described herein with reference to the accompanying drawings, wherein.

DETAILED DESCRIPTION OF EMBODIMENTS

Figure 1:
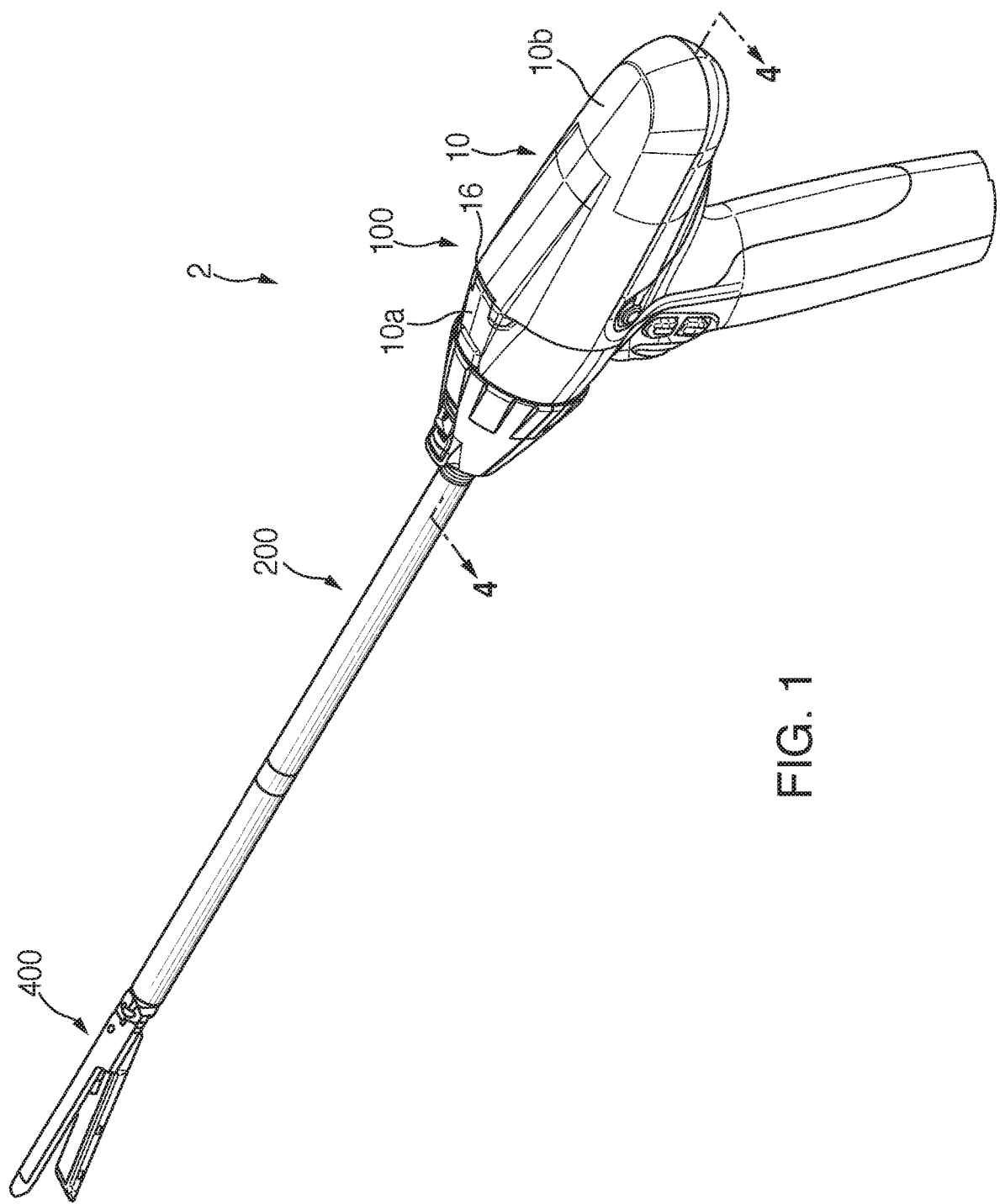
FIG. 1 is a perspective view of a surgical system including a handheld surgical device, an adapter assembly, and an end effector according to an embodiment of the present disclosure.

Embodiments of the presently disclosed surgical devices, and adapter assemblies for surgical devices and/or handle assemblies are described in detail with reference to the drawings, in which like reference numerals designate identical or corresponding elements in each of the several views. As used herein the term "distal" refers to that portion of the adapter assembly or surgical device, or component thereof, farther from the user, while the term "proximal" refers to that portion of the adapter assembly or surgical device, or component thereof, closer to the user.

The present disclosure provides an autoclavable load sensing device that may be disposed over any movable component (e.g., shaft) of a surgical device. The load sensing device is configured to measure the strain on the movable component and provide feedback to a controller of the surgical device. The load sensing device includes a housing and an insulated conductive element, e.g., an insulated electrical wire, disposed over the housing. The housing may be formed from any suitable compliant material that remains within its elastic range (e.g., avoiding permanent deflection) during deformation thereof while allowing for measurement of the strain. This allows the load sensing device to convert the load applied to it by the shaft into radial deflection. The redial deflection elongates the conductive element, thereby changing the electrical resistance of the conductive element. The conductive element may be formed from any conductive material capable of remaining within in its elastic range while it is deformed by the load sensing device.

The housing includes a tubular portion having a pair of opposing end caps disposed at each end thereof. Each of the end caps has a frustoconical shape having an opening at its tip allowing for the shaft to pass through each of the openings. Deflection of the shaft due to strain applies a force to the load sensing device. The tubular design of the load sensing device converts this force into radial deflection of the tubular portion. As the tubular portion is radially deflected, the conductive element wrapped around an annular groove defined in the tubular portion is also deformed and its electrical resistance increases, which is then sensed by a sensor circuit. The sensor circuit may include a Wheatstone bridge, which includes two parallel voltage divider circuits, with the conductive element forming one of the resistors of the Wheatstone bridge.

An adhesive or a potting material (e.g., epoxy) may be applied to the conductive element to secure it within the annular groove of the tubular portion. The adhesive may be applied as a layer around the conductive element to secure the conductive element to the load sensing device. However, even if the seal formed by the adhesive is broken, since the conductive element is insulated, functionality of the load sensing device would not be affected.

As illustrated in FIG. 1, a surgical system 2 according to the present disclosure includes a surgical device 100, which is shown as a powered hand held electromechanical instrument, configured for selective attachment to a plurality of different end effectors or single use loading units ("SULU's"), such as an end effector 400. In particular, surgical device 100 is configured for selective connection with an adapter 200, and, in turn, adapter 200 is configured for selective connection with the end effector 400.

Figure 6:
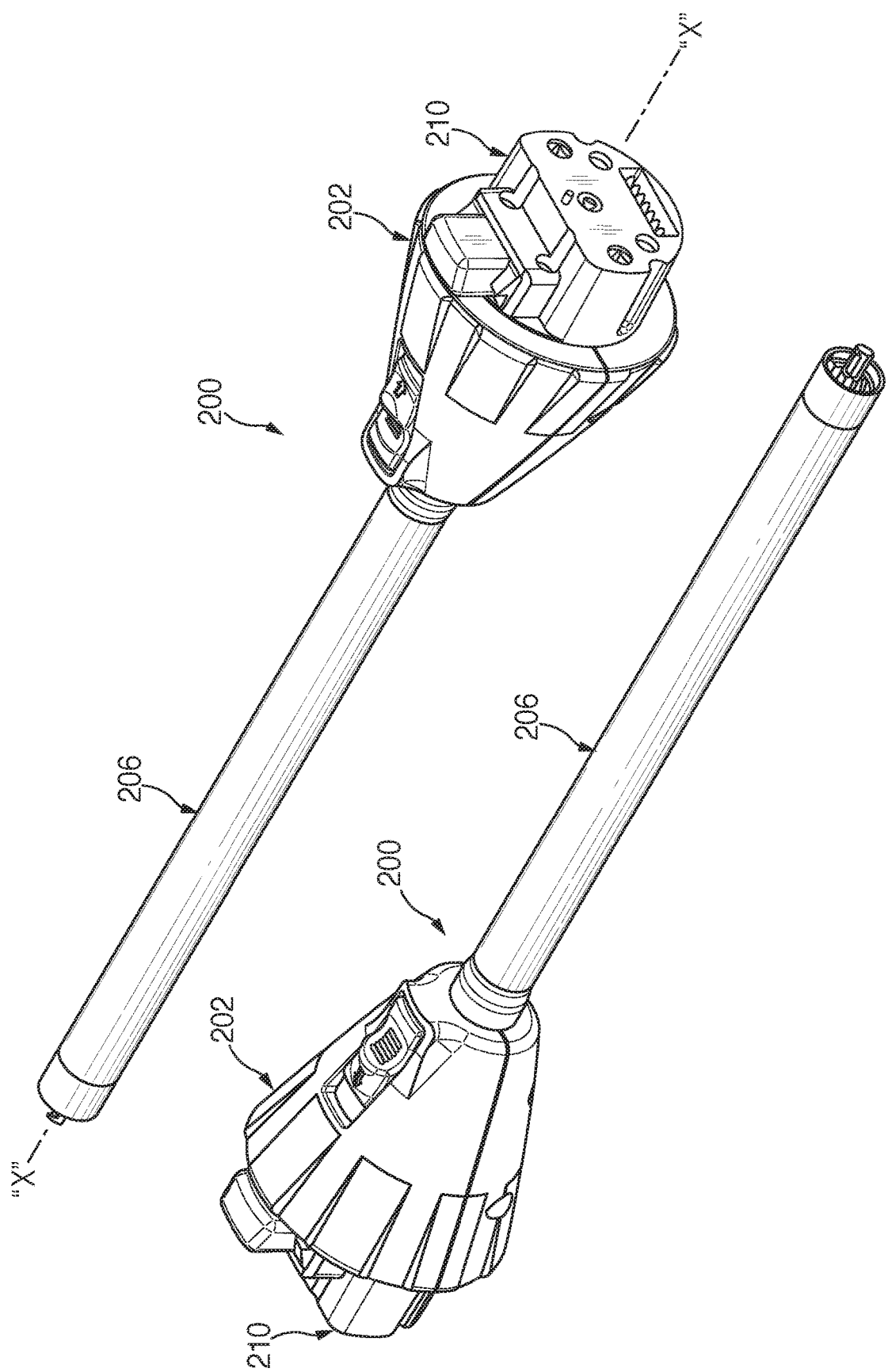
FIG. 6 is a front perspective view and a rear perspective view of the adapter assembly of FIG. 1.

With reference to FIGS. 1-4, surgical device 100 includes a power-pack 101 (FIG. 2), and an outer shell housing 10 configured to selectively receive and enclose the power-pack 101. Outer shell housing 10 includes a distal half-section 10a and a proximal half-section 10b. The proximal half-section 10b pivotably connected to distal half-section 10a by a hinge 16 located along an upper edge of distal half-section 10a and proximal half-section 10b such that distal and proximal half-sections 10a, 10b are divided along a plane that traverses a longitudinal axis "X" defined by adapter 200 (FIG. 6). When joined, distal and proximal half-sections 10a, 10b define a shell cavity 10c for receiving power-pack 101 inside.

Figure 2:
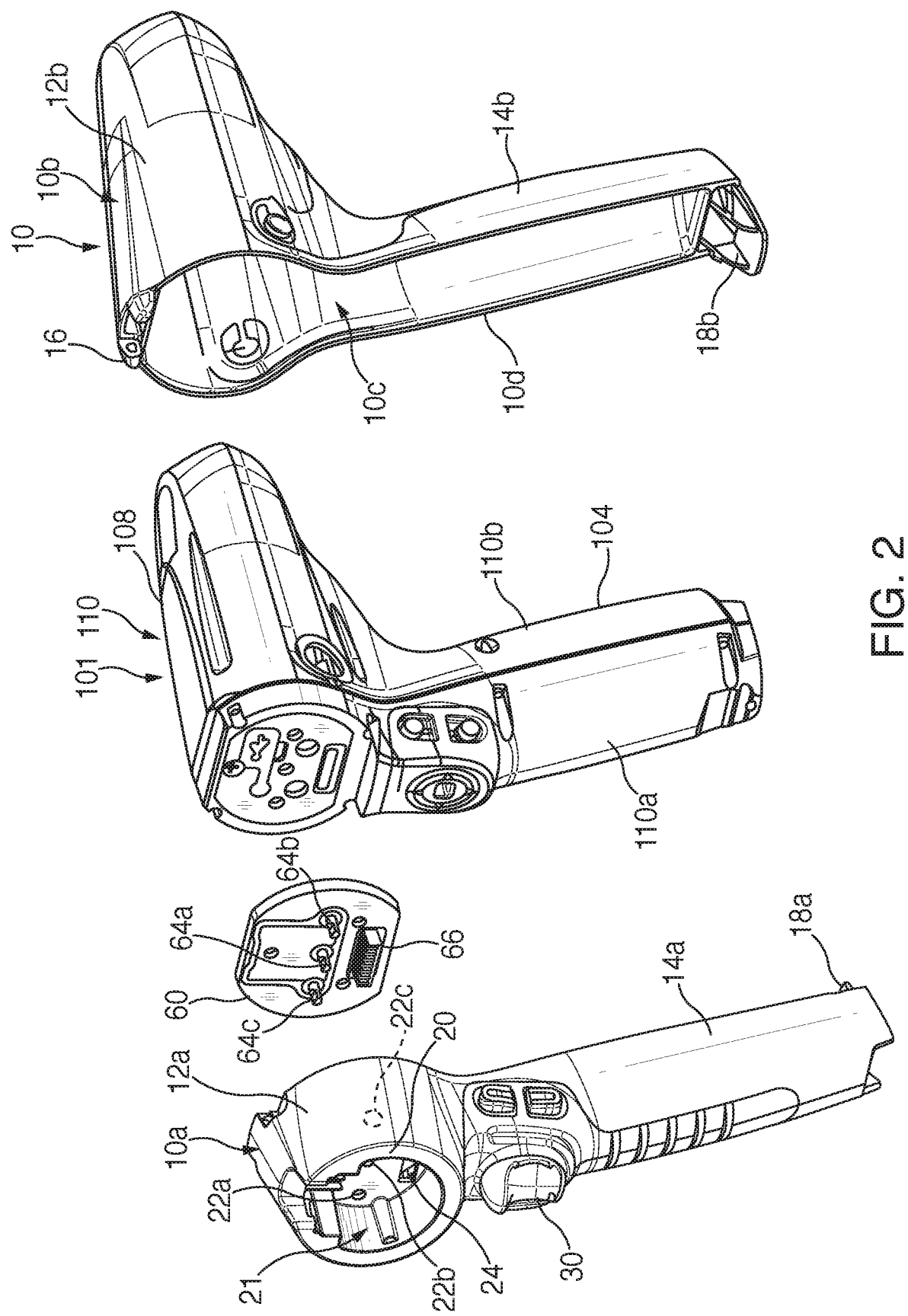
FIG. 2 is a front perspective view, with parts separated, of the handheld surgical device of FIG. 1.

With reference to FIG. 2, each of distal and proximal half-sections 10a, 10b includes a respective upper shell portion 12a, 12b, and a respective lower shell portion 14a, 14b. Lower shell portion 14a includes a closure tab 18a configured to engage a closure tab 18b of the lower shell portion 14b to selectively secure distal and proximal half-sections 10a, 10b to one another and for maintaining shell housing 10 in a closed configuration.

Figure 5:
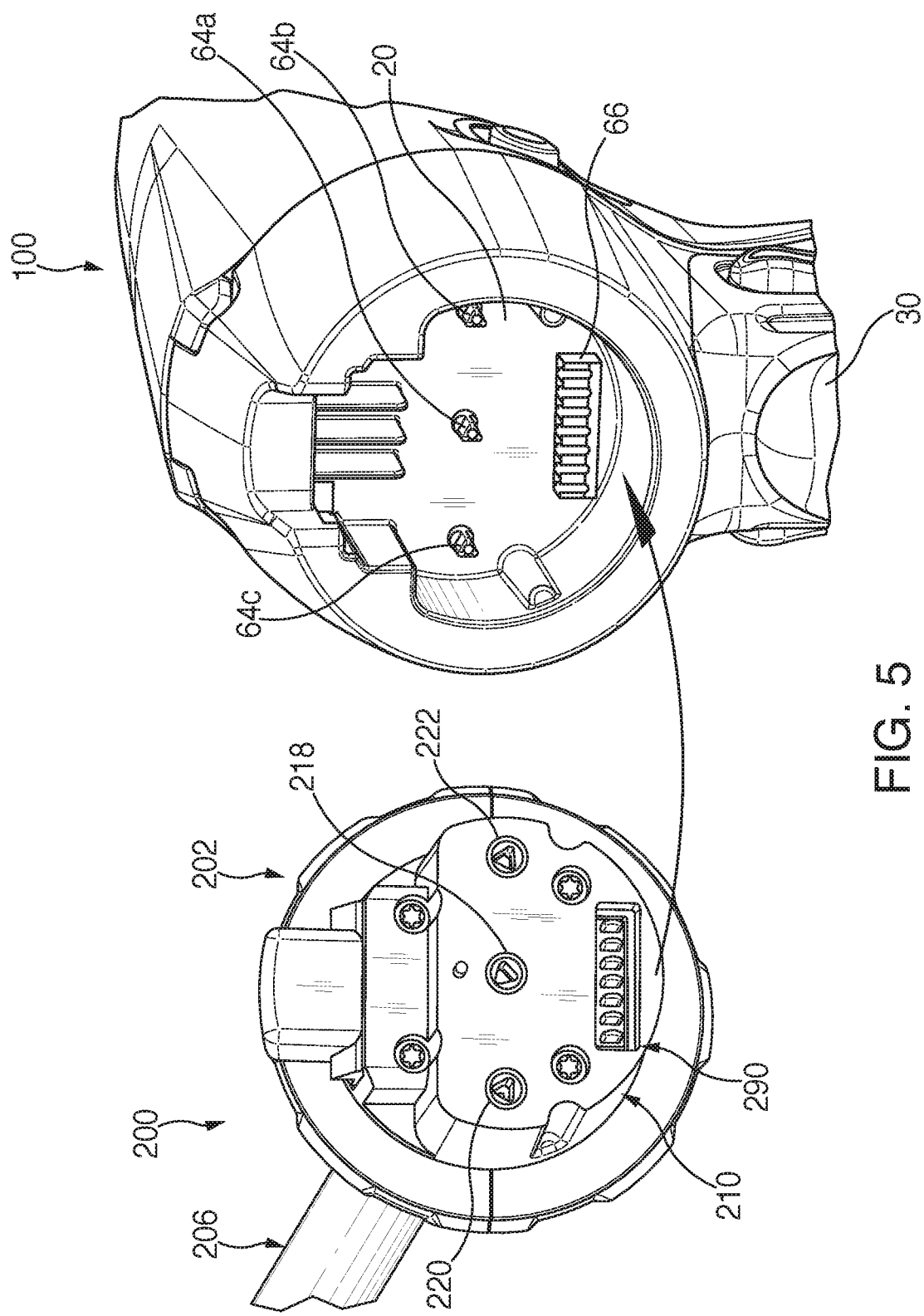
FIG. 5 is a perspective view illustrating a connection of the adapter assembly and the handheld surgical device of FIG. 1.

Distal half-section 10a of shell housing 10 also includes a connecting portion 20 configured to couple to a corresponding drive coupling assembly 210 of adapter 200 (FIGS. 5 and 6). Specifically, the connecting portion 20 includes a recess 21 configured to receive a portion of drive coupling assembly 210 of adapter 200 when adapter 200 is mated to surgical device 100. Connecting portion 20 of distal half-section 10a also defines three apertures 22a, 22b, 22c and an elongate slot 24 formed in a distally facing surface thereof.

Distal half-section 10a of shell housing 10 also includes a plurality of buttons such as a toggle control button 30. In embodiments, toggle control button 30 may be a two-axis control stick configured to be actuated in a left, right, up and down direction. The toggle control button 30 may also be depressible.

Distal half-section 10a of shell housing 10 may also support a plurality of other buttons such as a right-side pair of control buttons and a left-side pair of control button. These buttons and other components are described in detail in U.S. Patent Application Publication No. 2016/0310134, the entire disclosure of which is incorporated by reference herein.

With reference to FIG. 2, shell housing 10 includes a sterile barrier plate 60 removably supported in distal half-section 10a. The sterile barrier plate 60 interconnects the power-pack 101 and the adapter 200. Specifically, sterile barrier plate 60 is disposed behind connecting portion 20 of distal half-section 10a and within shell cavity 10c of shell housing 10. Plate 60 includes three coupling shafts 64a, 64b, 64c rotatably supported therein. Each coupling shaft 64a, 64b, 64c extends through a respective aperture 22a, 22b, 22c of connecting portion 20 of distal half-section 10a of shell housing 10.

Plate 60 further includes an electrical pass-through connector 66 supported thereon. Pass-through connector 66 extends through aperture 24 of connecting portion 20 of distal half-section 10a when sterile barrier plate 60 is disposed within shell cavity 10c of shell housing 10. Coupling shafts 64a, 64b, 64c and pass-through connector 66 electrically and mechanically interconnect respective corresponding features of adapter 200 and the power-pack 101.

During use, the shell housing 10 is opened (i.e., distal half-section 10a is separated from proximal half-section 10b about hinge 16), power-pack 101 is inserted into shell cavity 10c of shell housing 10, and distal half-section 10a is pivoted about hinge 16 to a closed configuration. In the closed configuration, closure tab 18a of lower shell portion 14a of distal half-section 10a engages closure tab 18b of lower shell portion 14b of proximal half-section 10b. Following a surgical procedure, shell housing 10 is opened and the power-pack 101 is removed from shell cavity 10c of shell housing 10. The shell housing 10 may be discarded and the power-pack 101 may then be disinfected and cleaned.

Figure 3:
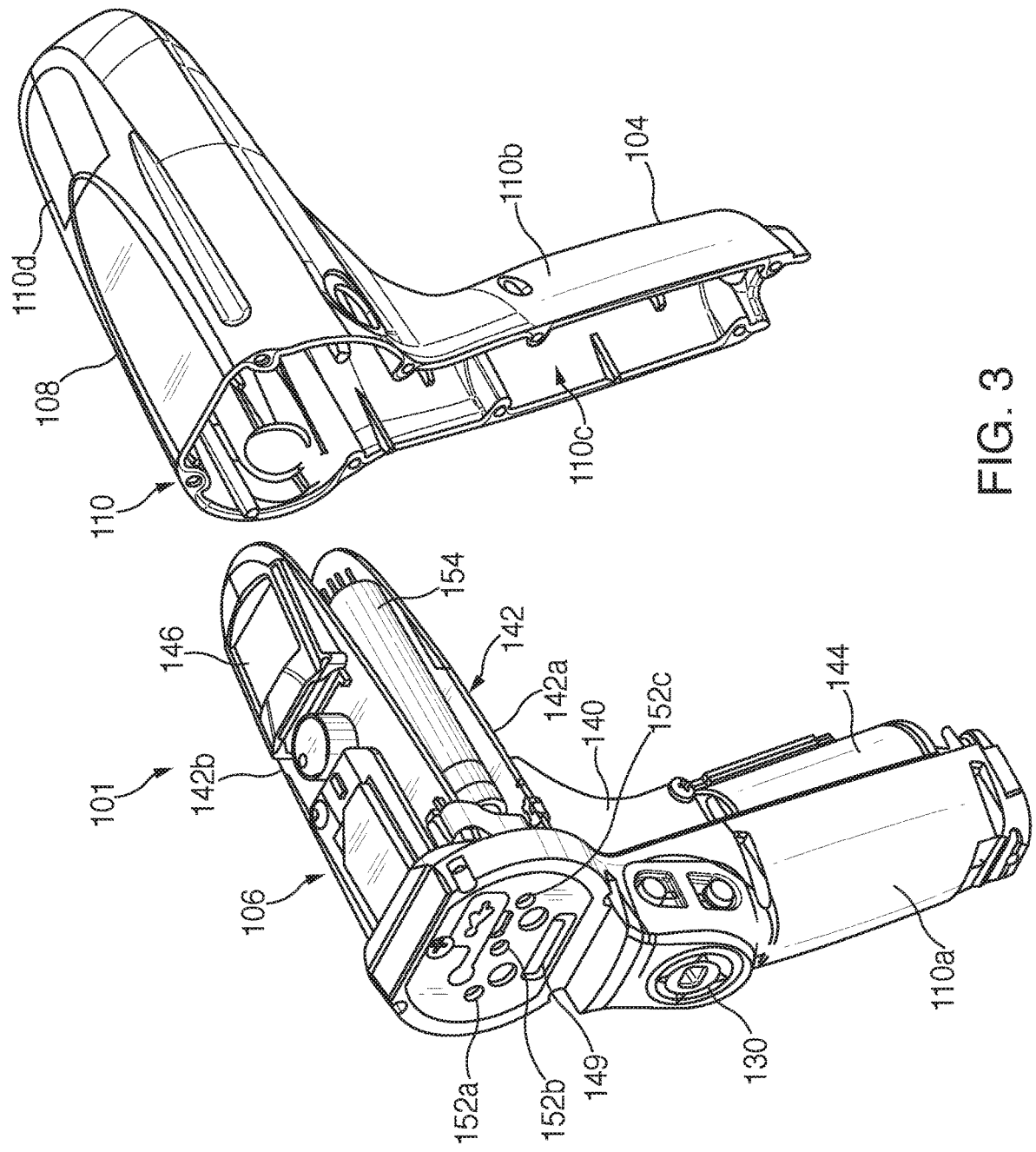
FIG. 3 is a front, perspective view of a power-pack and an inner rear housing separated therefrom.
Figure 4:
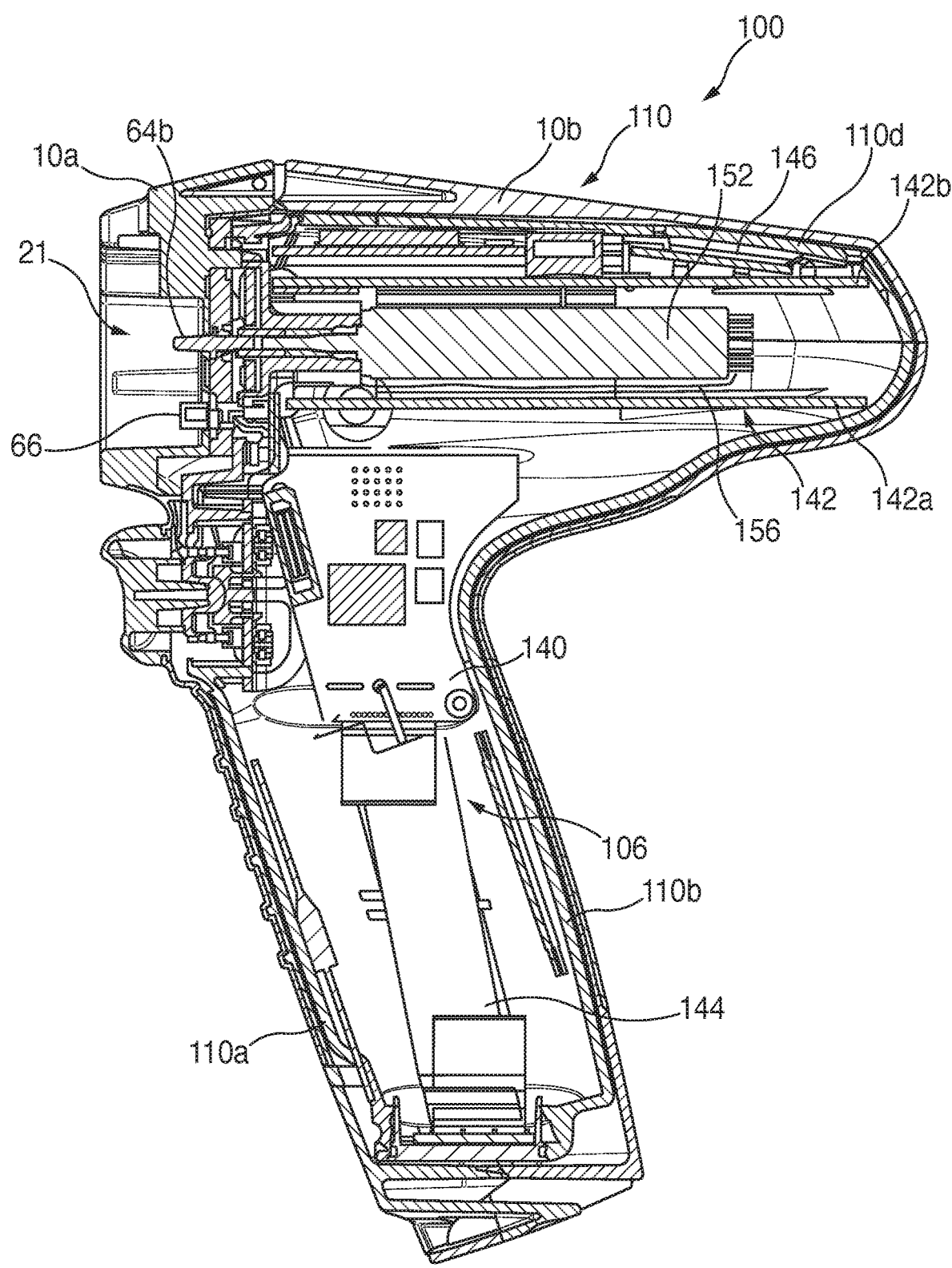
FIG. 4 is a cross-sectional view of the handheld surgical device of FIG. 2 taken along a section line "4-4"

Referring to FIGS. 2-4, power-pack 101 includes an inner handle housing 110 having a lower housing portion 104 and an upper housing portion 108 extending from and/or supported on lower housing portion 104. The inner handle housing 110 also includes a distal half-section 110a and a proximal half-section 110b, which define an inner housing cavity 110c (FIG. 3) for housing a power-pack core assembly 106 (FIG. 3). Power-pack core assembly 106 is configured to control the various operations of surgical device.

With reference to FIG. 3, distal half-section 110a of inner handle housing 110 supports a distal toggle control interface 130 that is operatively engaged with toggle control button 30 of shell housing 10, such that when power-pack 101 is disposed within shell housing 10, actuation of toggle control button 30 exerts a force on toggle control interface 130. Distal half-section 110a of inner handle housing 110 also supports various other control interfaces which operatively engage other buttons of shell housing 10.

With reference to FIGS. 3 and 4, power-pack core assembly 106 includes a battery circuit 140, a controller circuit board 142, and a rechargeable battery 144 configured to supply power to any of the electrical components of surgical device 100. Controller circuit board 142 includes a motor controller circuit board 142a, a main controller 142b, and a first ribbon cable (not shown) interconnecting motor controller circuit board 142a and main controller 142b.

Power-pack core assembly 106 further includes a display screen 146 supported on main controller 142b. Display screen 146 is visible through a clear or transparent window 110d disposed in proximal half-section 110b of inner handle housing 110.

Power-pack core assembly 106 further includes a first motor 152 (FIG. 4), a second motor 154 (FIG. 3), and a third motor 156 (FIG. 4) each electrically connected to controller circuit board 142 and battery 144. Motors 152, 154, 156 are disposed between motor controller circuit board 142a and main controller 142b. Each motor 152, 154, 156 is controlled by a respective motor controller (not shown) that are disposed on motor controller circuit board 142a and are coupled to the main controller 142b. The main controller 142b is also coupled to memory (not shown), which is also disposed on the main controller 142b. The main controller communicates with the motor controllers through an FPGA, which provides control logic signals (e.g., coast, brake, etc. and any other suitable control signals). The motor controllers output corresponding energization signals to their respective motors 152, 154, 156 using fixed-frequency pulse width modulation (PWM).

Power-pack core assembly 106 also includes an electrical receptacle 149. Electrical receptacle 149 is in electrical connection with main controller 142b via a second ribbon cable (not shown). Electrical receptacle 149 defines a plurality of electrical slots for receiving respective electrical contacts extending from pass-through connector 66 of plate 60 (FIG. 2) of shell housing 10.

Each motor 152, 154, 156 includes a respective motor shaft (not shown) extending therefrom. Each motor shaft may have a recess defined therein having a tri-lobe transverse cross-sectional profile for receiving proximal ends of respective coupling shaft 64a, 64b, 64c of plate 60 of shell housing 10.

Rotation of motor shafts by respective motors 152, 154, 156 actuate shafts and/or gear components of adapter 200 in order to perform the various operations of surgical device 100. In particular, motors 152, 154, 156 of power-pack core assembly 106 are configured to actuate shafts and/or gear components of adapter 200 in order to selectively actuate components of the end effector 400, to rotate end effector 400 about the longitudinal axis "X-X" (FIG. 6), and to pivot the end effector 400 about a pivot axis perpendicular to the longitudinal axis "X-X".

With reference to FIG. 5, when adapter 200 is mated to surgical device 100, each of coupling shafts 64a, 64b, 64c of plate 60 of shell housing 10 of surgical device 100 couples with corresponding rotatable connector sleeves 218, 220, 222 of adapter 200. Thus, rotation of each of coupling shafts 64a, 64b, 64c of surgical device 100 causes a corresponding rotation of the corresponding connector sleeve 218, 220, 222 of adapter 200.

With reference to FIGS. 5 and 6, adapter 200 includes an outer knob housing 202 and an outer tube 206 extending from a distal end of knob housing 202. Knob housing 202 is configured and adapted to connect to connecting portion 20 of shell housing 10 of surgical device 100. The outer tube 206 is configured for selective connection with end effector 400 (FIG. 1). Outer tube 206 is dimensioned for endoscopic insertion, e.g., being passable through a typical trocar port, cannula or the like, while the knob housing 202 is dimensioned to remain outside thereof.

Figure 7:
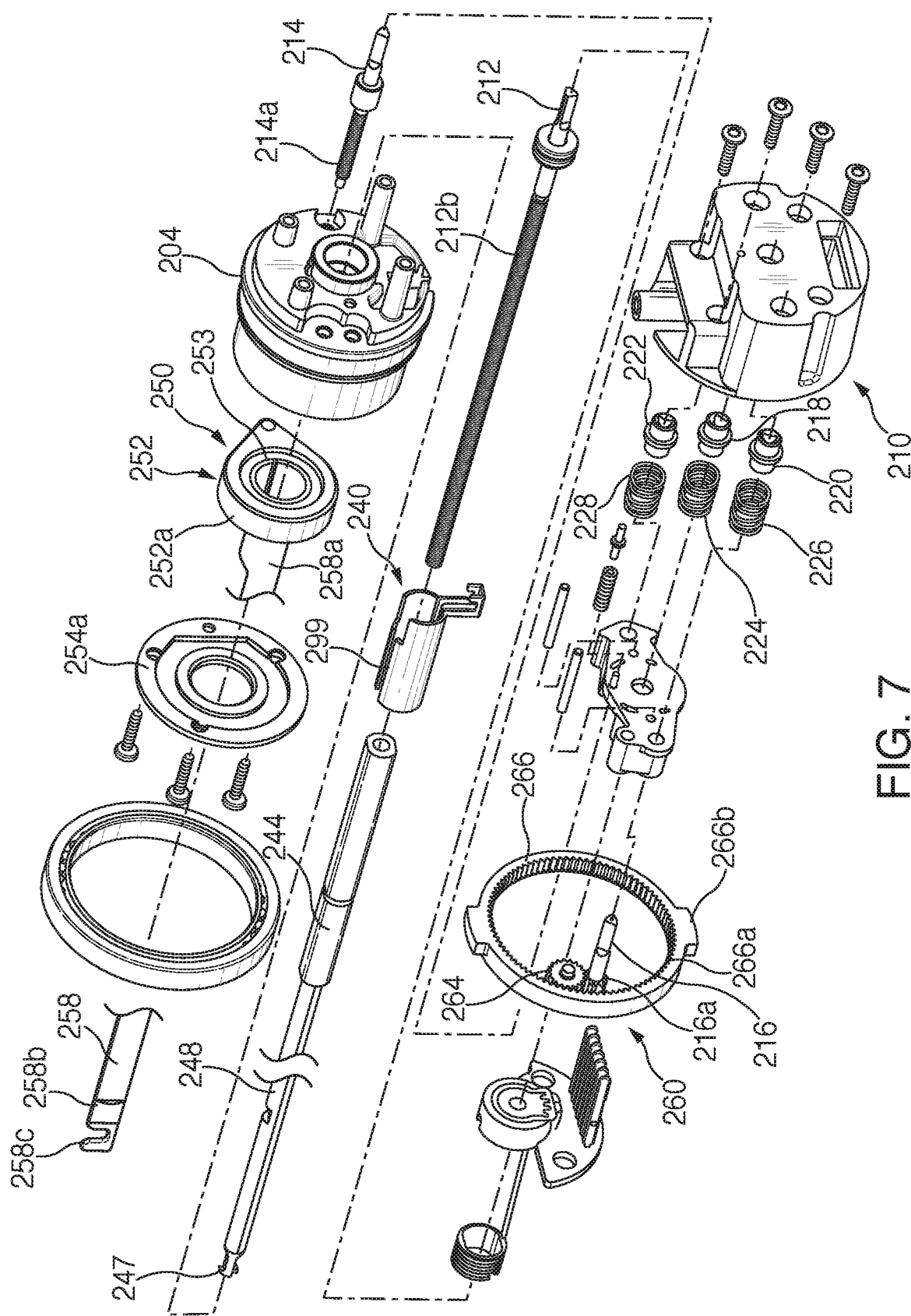
FIG. 7 is a rear, perspective view of the adapter assembly of FIG. 1 with parts separated.

As illustrated in FIG. 7, adapter 200 includes a proximal inner housing assembly 204 rotatably supporting a first rotatable proximal drive shaft 212, a second rotatable proximal drive shaft 214, and a third rotatable proximal drive shaft 216 therein. Each proximal drive shaft 212, 214, 216 transmits rotational forces from respective coupling shafts 64a, 64b and 64c (FIG. 5) of surgical device 100, as described in greater detail below.

Drive coupling assembly 210 of adapter 200 is also configured to rotatably support first, second and third connector sleeves 218, 222, 220, respectively, arranged in a common plane or line with one another. Each of connector sleeves 218, 222, 220 is configured to interconnect respective first, second and third coupling shafts 64a, 64b, 64c of surgical device 100 with first, second and third proximal drive shafts 212, 214, 216 of adapter 200.

Drive coupling assembly 210 of adapter 200 also includes a first, a second, and a third biasing member 224, 226, 228 disposed distally of respective first, second, and third connector sleeves 218, 220, 222. Each of biasing members 224, 226, 228 is disposed about respective first, second and third rotatable proximal drive shaft 212, 214, 216. Biasing members 224, 226, 228 act on respective connector sleeves 218, 222, 220 and maintain connector sleeves 218, 222, 220 engaged with the distal end of respective coupling shafts 64a, 64c, 64b (FIG. 5) of surgical device 100 when adapter 200 is connected to surgical device 100.

Adapter 200 also includes a first, a second and a third rotation conversion assembly 240, 250, 260, respectively, disposed within inner housing assembly 204 and outer tube 206. First rotation conversion assembly 240 converts rotation of first coupling shaft 64a of surgical device 100 into axial translation of articulation bar 258 of adapter 200 to effectuate articulation of end effector 400. First rotation conversion assembly 240 includes first rotatable proximal drive shaft 212, which is rotatably supported within inner housing assembly 204. First rotatable proximal drive shaft 212 includes a proximal end portion configured for connection with first connector 218 which is connected to respective first coupling shaft 64a of surgical device 100. First rotatable proximal drive shaft 212 also includes a distal end portion 212b having a threaded outer profile or surface.

First rotation conversion assembly 240 further includes a drive coupling nut 244 rotatably coupled to threaded distal end portion 212b of first rotatable proximal drive shaft 212, and which is slidably disposed within outer tube 206 (FIG. 6). Drive coupling nut 244 is slidably keyed within proximal portion of outer tube 206 so as to be prevented from rotation as first rotatable proximal drive shaft 212 is rotated. Thus, as first rotatable proximal drive shaft 212 is rotated, drive coupling nut 244 is translated along threaded distal end portion 212b of first rotatable proximal drive shaft 212 and, in turn, through and/or along outer tube 206.

First rotation conversion assembly 240 further includes a distal drive member 248 that is mechanically engaged with drive coupling nut 244, such that axial movement of drive coupling nut 244 results in a corresponding amount of axial movement of distal drive member 248 to effectuate closing, opening and firing of end effector 400. A distal end portion of distal drive member 248 supports a connection member 247 configured and dimensioned for selective engagement with a drive member (not shown) of end effector 400. Drive coupling nut 244 and/or distal drive member 248 function as a force transmitting member to components of end effector 400.

Second conversion assembly 250 converts rotation of second coupling shaft 64b of surgical device 100 into axial translation of a articulation bar 258 of adapter 200 to effectuate articulation of end effector 400. Second drive converter assembly 250 of adapter 200 includes second proximal drive shaft 214 rotatably supported within inner housing assembly 204. Second rotatable proximal drive shaft 214 includes a proximal end portion configured for connection with second connector 222 (FIG. 5) which is connected to second coupling shaft 64c of surgical device 100. Second rotatable proximal drive shaft 214 further includes a distal end portion 214a having a threaded outer profile or surface.

Distal end portion 214a of proximal drive shaft 214 is threadably engaged with an articulation bearing housing 252a of an articulation bearing assembly 252. Articulation bearing assembly 252 is both rotatable and longitudinally translatable within outer tube 206. Articulation bearing assembly 252 includes a housing 252a supporting an articulation bearing 253. Articulation bearing housing 252a has a non-circular outer profile, e.g., tear-drop shape, that is slidably and non-rotatably disposed within a complementary bore (not shown) of inner housing assembly 204.

Second drive converter assembly 250 of adapter 200 further includes an articulation bar 258 having a proximal portion 258a secured to articulation bearing 253. A distal portion 258b of articulation bar 258 includes a slot 258c therein, which is configured to couple to an articulation link (not shown) of end effector 400.

Third conversion assembly 260 converts rotation of third coupling shaft 64c (FIG. 5) of surgical device 100 into rotation of a rotation ring gear 266 of adapter 200, to effectuate rotation of adapter 200. The rotation ring gear 266 is fixedly supported in and connected to outer knob housing 202 (FIGS. 5 and 6). Ring gear 266 defines an internal array of gear teeth 266a and a pair of diametrically opposed, radially extending protrusions 266b projecting from an outer edge thereof. Protrusions 266b are disposed within recesses (not shown) defined in outer knob housing 202, such that rotation of ring gear 266 results in rotation of outer knob housing 202, and vice a versa.

Third rotation conversion assembly 260 further includes third rotatable proximal drive shaft 216, which is rotatably supported within inner housing assembly 204. Third rotatable proximal drive shaft 216 includes a proximal end portion configured for connection with third connector 220 to a third rotatable proximal drive shaft 216, which includes a spur gear 216a keyed to a distal end thereof. A reversing spur gear 264 engages spur gear 216a of third rotatable proximal drive shaft 216 to the ring gear 266.

As third rotatable proximal drive shaft 216 is rotated by the third coupling shaft 64b of surgical device 100, spur gear 216a of third rotatable proximal drive shaft 216 engages reversing gear 264 causing reversing gear 264 to rotate. As reversing gear 264 rotates, ring gear 266 also rotates thereby causing outer knob housing 202 to rotate, thus rotating the outer tube 206 along with the end effector 400 about longitudinal axis "X-X".

Figure 8:
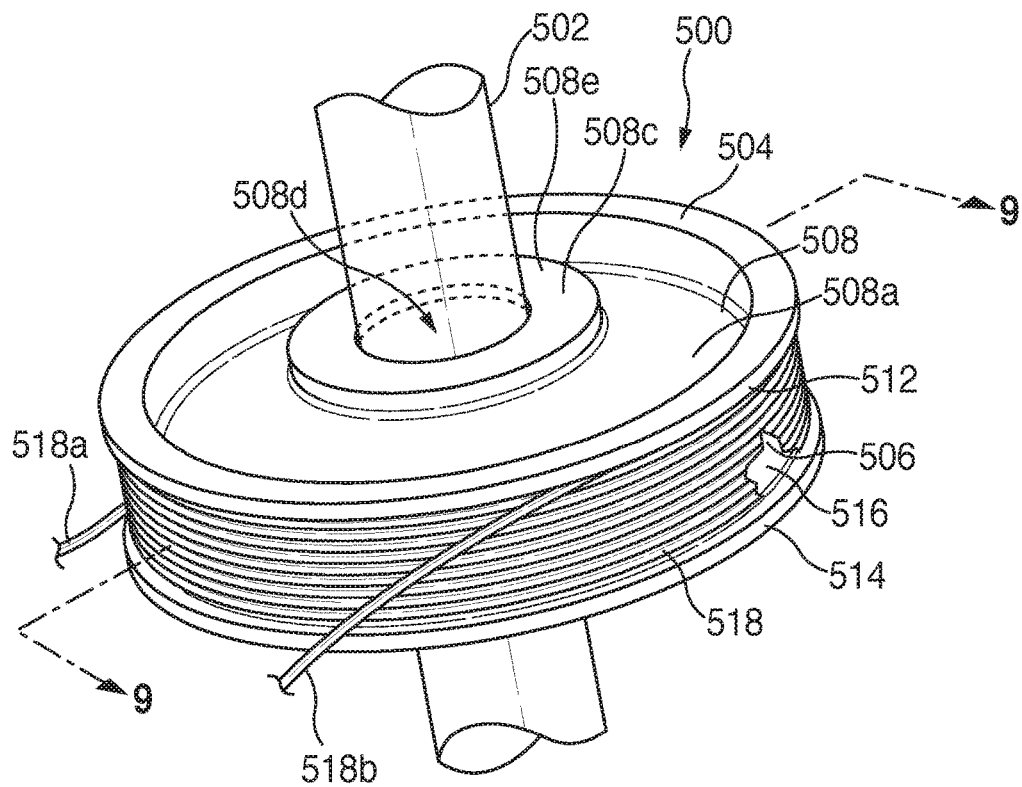
FIG. 8 is a perspective view of an autoclavable load sensing device according to an embodiment of the present disclosure.
Figure 9:
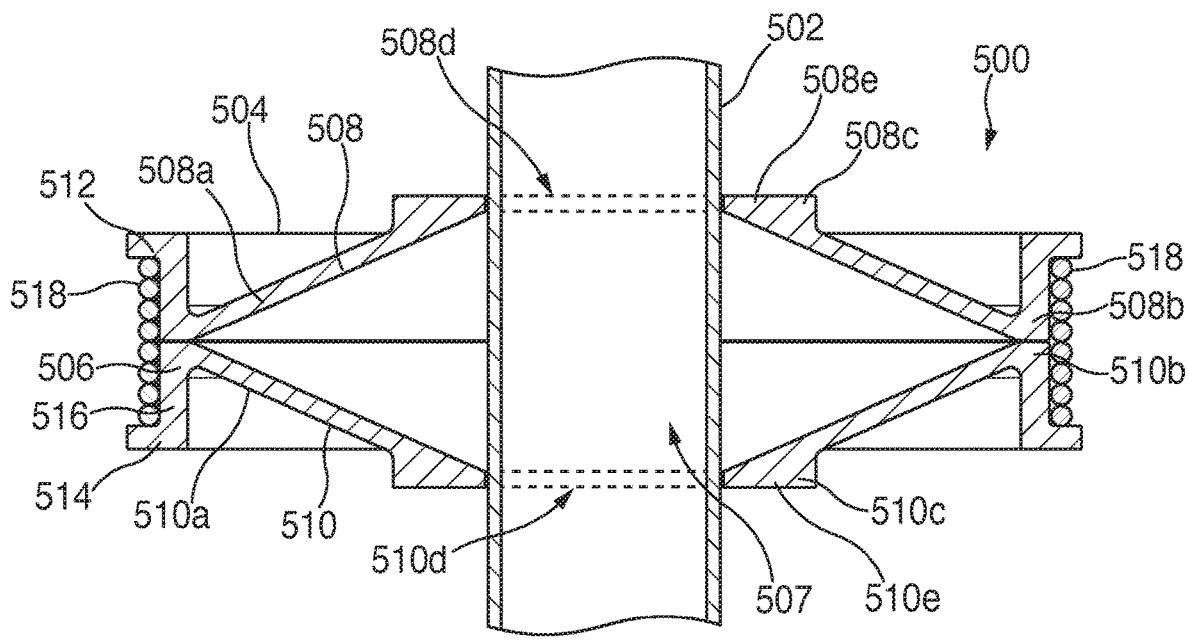
FIG. 9 is a cross-sectional view of the autoclavable load sensing device of FIG. 8 taken along a section line "9-9"

With reference to FIGS. 8 and 9, a load sensing device 500 according to the present disclosure is disposed over a shaft 502, which may be any of the drive shafts 212, 214, 216 of the adapter 200. In particular, the shaft 502 passes through the load sensing device 500 such the load sensing device 500 is configured to measure strain on the shaft 502.

The load sensing device 500 includes a housing 504 having a tubular portion 506 and a pair of opposing end caps, a first end cap 508 and a second end cap 510. Each of the first and second end cap portions 508 and 510 includes a frustoconical wall 508a and 510a extending between its respective base 508b and 510b (FIG. 9) and respective tip portion 508c and 510c. As used herein, the term "frustoconical" denotes a cone whose tip has been truncated by a plane parallel to the cone's base. Each of the first and second end cap portions 508 and 510 also includes an opening 508d and 510d defined through the respective tip portions 508c and 510c. The housing 504 defines a cavity 507 disposed between the tip portions 508c and 510c, which is accessible through the openings 508d and 510d. The shaft 502 passes through the openings 508d and 510d and the cavity 507 (FIG. 9).

The load sensing device 500 may be secured to the shaft 502 by any suitable methods, such as ultrasonic welding, laser welding, or adhesives. In embodiments, the tip portions 508c and 510c may include a flat portion 508e and 510e, which act as washers when being coupled to the shaft 502, such that load sensing device 500 may be secured to the shaft using a pair of opposing fixating members (e.g., nuts) disposed at each flat portion 508e and 510e. Fixation of the load sensing device 500 to the shaft 502 ensures that the strain imparted on the shaft 502 is imparted on the load sensing device 500, allowing for the measurement of the strain on the shaft 502.

In embodiments, the load sensing device 500 may be formed as a unitary part (e.g., injection molding, 3D printing, machining, or the like) or by joining separately-formed components together, such as the tubular portion 506, the first end cap 508, the second cap 510. The components may be joined by any suitable methods, such as by ultrasonic welding, laser welding, or adhesives. The load sensing device 500 may be formed from any suitable material that remains within the elastic range (e.g., avoiding permanent deflection during deflection thereof) while allowing for measurement of the strain. Suitable materials include thermoplastics, such as acrylics, celluloid, cellulose acetate, cyclic olefin copolymer, ethylene-vinyl acetate, fluoropolymers (e.g., polytetrafluoroethylene), ionomers, polyoxymethylene, polyacrylates, polyacrylonitrile, polyamide, polyamide-imide, polyaryletherketon, polybutadiene, polybutylene, polybutylene terephthalate, polycaprolactone, polychlorotrifluoroethylene, polyethylene terephthalate, polycyclohexylene dimethylene terephthalate, polycarbonate, polyhydroxyalkanoates, polyketones, polyester, polyethylene, polyetheretherketone, polyetherketoneketone, polyetherimide, polyethersulfone, chlorinated polyethylene, polyimide, polylactic acid, polymethylpentene, polyphenylene oxide, polyphenylene sulfide, polyphthalamide, polypropylene, polystyrene, polysulfone, polytrimethylene terephthalate, polyurethane, polyvinyl acetate, polyvinyl chloride, polyvinylidene chloride, styrene-acrylonitrile, and combinations thereof.

The tubular portion 506 includes a pair of radially extending lips 512 and 514 around the tubular portion 506 and defining an annular groove 516. The load sensing device 500 also includes a conductive element 518 disposed within the annular groove 516. The conductive element 518 may be a wire formed from any suitable conductive metal that also remains within in its elastic range during deformation by the load sensing device 500, such as copper, aluminum, tungsten, gold, silver, and combinations thereof. The conductive element 518 may be wrapped about the circumference of the annular groove 516 partially (e.g., quarter, half, etc. of a turn) or any number of turns. The turns of the conductive element 518 may be wrapped in the same direction or may alternate. The conductive element 518 may be encased in an insulative sheath (not shown) that covers the conductive element. In this manner, potting material (e.g., epoxy) or an adhesive may be used to fill the annular groove 516 thereby securing the conductive element 518 therein.

Figure 10:
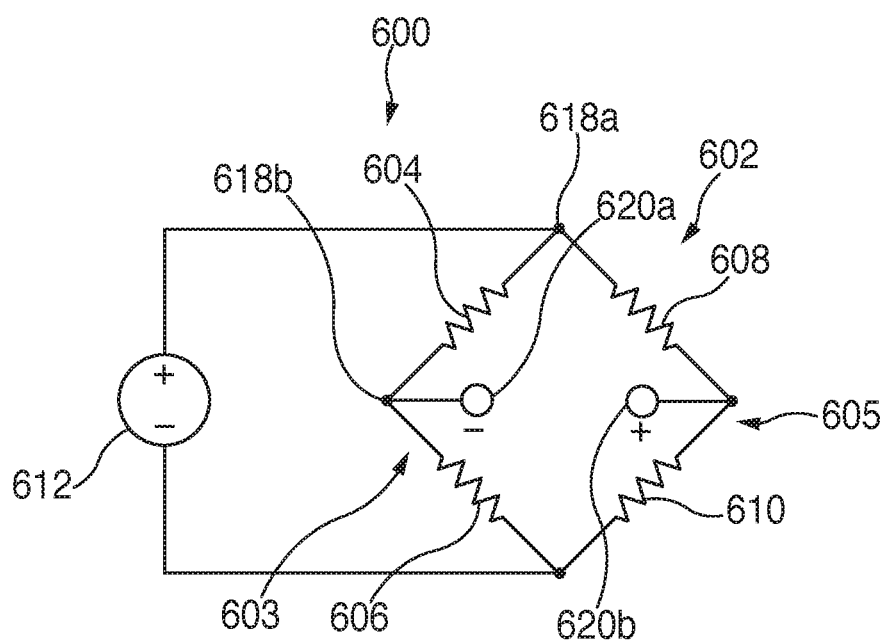
FIG. 10 is a schematic electrical diagram of a strain sensor circuit according to an embodiment of the present disclosure.

The conductive element 518 includes a first end 518a and a second end 518b (FIG. 8), which are coupled to a strain sensor circuit 600 as shown in FIG. 10. The strain sensor circuit 600 includes a resistor network 602 (e.g., Wheatstone bridge) having two parallel voltage divider circuits, namely, a first voltage divider circuit 603 having the resistive arms 604 and 606 and a second voltage divider circuit 605 having the resistive arms 608 and 610. The first and second voltage divider networks 603 and 605 are coupled to a voltage source 612 that supplies an electrical current to the resistor network 602. In embodiments, the voltage source 612 may be the rechargeable battery 144 (FIGS. 3 and 4). The conductive element 518 may be any one of the four resistive arms 604, 606, 608, or 610 and in an exemplary embodiment is shown as the resistive arm 604 with the first and second ends 518a and 518b coupled at nodes 618a and 618b of the resistor network 602. The resistor network 602 also includes a pair of output terminals 620a and 620b coupled to the controller circuit board 142 (FIG. 3), and in particular, the main controller 142b (FIG. 3).

During use, as the conductive element 518 is deformed due to the strain on the load sensing device 500, the resistance of the conductive element 518 (e.g., the resistive arm 604) changes as well. The resistor network 602 is calibrated to output zero voltage when the resistance of the first and second voltage divider networks 603 and 605 is the same. However, once the resistance of the first voltage divider network 603 is modified due to the change in the resistance of the conductive element 518 (e.g., the resistive arm 604), the output of the resistor network 602 is changed as well. Thus, any change in the resistance of the conductive element 518 results in a nonzero output voltage from the output terminals 620a and 620b, which is a function of the strain on the load sensing device 500 imparted by the shaft 502. The output is transmitted through the connector 290 (FIG. 5) to the main controller 142b (FIGS. 3 and 4), which then converts and/or otherwise calculates the strain based on the output of the resistor network 602. The connector 290 also couples the strain sensor circuit 600 to the battery 144, allowing the battery 144 to supply electrical current to the strain sensor circuit 600.

It will be understood that various modifications may be made to the embodiments of the presently disclosed adapter assemblies. Therefore, the above description should not be construed as limiting, but merely as exemplifications of embodiments. Those skilled in the art will envision other modifications within the scope and spirit of the present disclosure.

What is claimed is:

1. A load sensing device comprising:
   a housing including:
      a tubular portion having an outer wall, a longitudinally extending inner wall, a first end, and a second end and defining a cavity between the first end and the second end;
      a radially extending lip extending perpendicular to the longitudinally extending inner wall;
      a first end cap disposed at the first end, the first end cap having a first opening; and
      a second end cap disposed at the second end, the second end cap having a second opening; and
   a conductive element wrapped at least partially about the outer wall of the tubular portion.

2. The load sensing device according to claim 1, wherein each of the first end cap and the second end cap has a frustoconical shape.

3. The load sensing device according to claim 1, further comprising a second radially extending lip, wherein an annular groove is defined between the radially extending lip and the second radially extending lip.

4. The load sensing device according to claim 3, wherein the conductive element is disposed within the annular groove.

5. The load sensing device according to claim 4, further comprising a potting material disposed within the annular groove.

6. The load sensing device according to claim 4, wherein the conductive element includes an insulative sheath.

7. An adapter for interconnecting a surgical end effector to a surgical device, the adapter including:
   a drive shaft; and
   a load sensing device disposed about the drive shaft, the load sensing device configured to measure strain imparted on the drive shaft, the load sensing device including:
      a housing having:
         a tubular portion having an outer wall, a longitudinally extending inner wall, a first end, and a second end and defining a cavity between the first end and the second end;
         a radially extending lip extending perpendicular to the longitudinally extending inner wall;
         a first end cap disposed at the first end, the first end cap having a first opening; and
         a second end cap disposed at the second end, the second end cap having a second opening; and
      a conductive element wrapped at least partially about the outer wall of the tubular portion.

8. The adapter according to claim 7, wherein each of the first end cap and the second end cap has a frustoconical shape.

9. The adapter according to claim 7, further comprising a second radially extending lip, wherein an annular groove is defined between the radially extending lip and the second radially extending lip.

10. The adapter according to claim 9, wherein the conductive element is disposed within the annular groove.

11. The adapter according to claim 9, further comprising a potting material disposed within the annular groove.

12. The adapter according to claim 11, wherein the conductive element includes an insulative sheath.

13. The adapter according to claim 7, further comprising:
   a strain sensor circuit coupled to the conductive element, the strain sensor circuit configured to output an electrical signal corresponding to the strain imparted on the drive shaft.

14. The adapter according to claim 13, wherein the strain sensor circuit includes a resistor network having a plurality of resistive arms.

15. The adapter according to claim 14, wherein the conductive element is one of the plurality of resistive arms.

16. A surgical system comprising:
   a handheld surgical device including a motor, a power source coupled to the motor, and a controller configured to control the motor; and
   an adapter configured to couple to the surgical device, the adapter including:
      a drive shaft configured to couple to and movable by the motor; and
      a load sensing device disposed about the drive shaft, the load sensing device configured to measure strain imparted on the drive shaft, the load sensing device including:
         a housing having:
            a tubular portion having an outer wall, a longitudinally extending inner wall, a first end, and a second end and defining a cavity between the first end and the second end;
            a radially extending lip extending perpendicular to the longitudinally extending inner wall;
            a first end cap disposed at the first end, the first end cap having a first opening; and
            a second end cap disposed at the second end, the second end cap having a second opening; and
         a conductive element wrapped at least partially about the outer wall of the tubular portion.

17. The surgical system according to claim 16, wherein the adapter further includes:
   a strain sensor circuit coupled to the conductive element, the strain sensor circuit configured to output an electrical signal corresponding to the strain imparted on the drive shaft.

18. The surgical system according to claim 17, wherein the strain sensor circuit includes a resistor network having a plurality of resistive arms.

19. The surgical system according to claim 18, wherein the conductive element is one of the plurality of resistive arms.

20. The surgical system according to claim 17, wherein the strain sensor circuit is configured to couple to the power source.

* * * * *